US00PP17459P2

(12) United States Plant Patent
Post

(10) Patent No.: US PP17,459 P2
(45) Date of Patent: Feb. 27, 2007

(54) ***CHRYSANTHEMUM* PLANT NAMED 'SAMOS'**

(50) Latin Name: *Chrysanthemum×morifolium*
Varietal Denomination: Samos

(75) Inventor: Arie Gerard Post, Delft (NL)

(73) Assignee: Deliflor Royalties B.V., Maasdijk (NL)

( * ) Notice: Subject to any disclaimer, the term of this patent is extended or adjusted under 35 U.S.C. 154(b) by 21 days.

(21) Appl. No.: 11/171,807

(22) Filed: Jun. 30, 2005

(51) Int. Cl.
*A01H 5/00* (2006.01)

(52) U.S. Cl. ..... Plt./294

(58) Field of Classification Search ..... Plt./294
See application file for complete search history.

(56) References Cited

U.S. PATENT DOCUMENTS

2005/0177911 P1 * 8/2005 Lintott ..... Plt./294

* cited by examiner

*Primary Examiner*—Wendy Haas
(74) *Attorney, Agent, or Firm*—C. A. Whealy

(57) ABSTRACT

A new and distinct cultivar of *Chrysanthemum* plant named 'Samos', characterized by its anemone-type inflorescences with white-colored ray florets and red purple-colored disc florets; freely flowering habit; early and uniform flowering response; and good postproduction longevity.

1 Drawing Sheet

Botanical designation: *Chrysanthemum×morifolium.*
Cultivar denomination: 'Samos'.

BACKGROUND OF THE INVENTION

The present invention relates to a new and distinct cultivar of *Chrysanthemum* plant, botanically known as *Chrysanthemum×morifolium* and referred to by the name 'Samos'.

The new *Chrysanthemum* is the product of a planned breeding program conducted by the Inventor in 's Gravenzande, The Netherlands. The objective of the breeding program is to create new vigorous cut *Chrysanthemum* cultivars with interesting inflorescence forms and attractive floret coloration.

The new *Chrysanthemum* originated from a cross-pollination on Mar. 14, 2001 in 's Gravenzande, The Netherlands, of a proprietary seedling selection of *Chrysanthemum×morifolium* identified as code number 6635, not patented, as the female, or seed, parent with a proprietary seedling selection of *Chrysanthemum×morifolium* identified as code number 4441, not patented, as the male, or pollen, parent. The new *Chrysanthemum* was discovered and selected by the Inventor as a single plant within the progeny of the stated cross-pollination in a controlled environment in 's Gravenzande, The Netherlands.

Asexual reproduction of the new *Chrysanthemum* by terminal cuttings in a controlled environment in 's Gravenzande, The Netherlands since Apr. 23, 2002, has shown that the unique features of this new *Chrysanthemum* are stable and reproduced true to type in successive generations.

BRIEF SUMMARY OF THE INVENTION

The cultivar Samos has not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'Samos'. These characteristics in combination distinguish 'Samos' as a new and distinct cultivar:

1. Anemone-type inflorescences with white-colored ray florets and red purple-colored disc florets; typically grown as a spray-type.
2. Vigorous growth habit.
3. Freely flowering habit.
4. Early and uniform flowering response.
5. Good postproduction longevity.

Plants of the new *Chrysanthemum* can be compared to plants of the female parent selection. In side-by-side comparisons conducted in 's Gravenzande, The Netherlands, plants of the new *Chrysanthemum* differed from plants of the female parent selection in the following characteristics:

1. Plants of the new *Chrysanthemum* were more freely flowering than plants of the female parent selection.
2. Plants of the new *Chrysanthemum* had lighter green-colored leaves than plants of the female parent selection.
3. Plants of the new *Chrysanthemum* had lighter red purple-colored disc florets than plants of the female parent selection.

Plants of the new *Chrysanthemum* can be compared to plants of the male parent selection. In side-by-side comparisons conducted in 's Gravenzande, The Netherlands, plants of the new *Chrysanthemum* differed from plants of the male parent selection in the following characteristics:

1. Plants of the new *Chrysanthemum* flowered about three to four days earlier than plants of the male parent selection.
2. Plants of the new *Chrysanthemum* had smaller inflorescences than plants of the male parent selection.

3. Plants of the new *Chrysanthemum* and the male parent selection differed in ray floret coloration as plants of the male parent selection had orange-colored ray florets.

Plants of the new *Chrysanthemum* can be compared to plants of the *Chrysanthemum* cultivar Jo Spithoven, not patented. In side-by-side comparisons conducted in 's Gravenzande, The Netherlands, plants of the new *Chrysanthemum* differed primarily from plants of the cultivar Jo Spithoven in the following characteristics:

1. Plants of the new *Chrysanthemum* were more vigorous and stronger than plants of the cultivar Jo Spithoven.
2. Plants of the new *Chrysanthemum* flowered about one week earlier than plants of the cultivar Jo Spithoven.
3. Plants of the new *Chrysanthemum* and the cultivar Jo Spithoven differed in disc floret coloration as plants of the cultivar Jo Spithoven had darker red purple-colored disc florets.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ slightly from the color values cited in the detailed botanical description which accurately describe the actual colors of the new *Chrysanthemum.*

The photograph at the top of the sheet comprises a side perspective view of a typical flowering stem of 'Samos'.

The photograph in the middle of the sheet is a close-up view of typical inflorescences of 'Samos'.

The photograph at the bottom of the sheet is a close-up view of upper (left) and lower (right) surfaces of typical inflorescences and typical leaves of 'Samos'.

DETAILED BOTANICAL DESCRIPTION

In the following description, color references are made to The Royal Horticultural Society Colour Chart, 2001 Edition, except where general terms of ordinary dictionary significance are used. The aforementioned photographs and following observations and measurements describe plants grown during the winter and early spring in 's Gravenzande, The Netherlands, under commercial practice in a glass-covered greenhouse. Plants were initially given long day/short night treatments followed by short day/long night treatments to induce flower initiation and development. During the production of the plants, day temperatures averaged 18° C., night temperatures averaged 17° C. and light levels were about 4,000 lux. Plants were grown as spray-types and were about ten weeks from planting when the photographs and the description were taken.

Botanical classification: *Chrysanthemum×morifolium* cultivar Samos.

Commercial classification: Anemone-type *Chrysanthemum* typically grown as a spray-type cut flower.

Parentage:

*Female, or seed, parent.*—Proprietary seedling selection of *Chrysanthemum×morifolium* identified as code number 6635, not patented.

*Male, or pollen, parent.*—Proprietary seedling selection of *Chrysanthemum×morifolium* identified as code number 4441, not patented.

Propagation:

*Type.*—Terminal tip cuttings.

*Time to initiate roots, summer.*—About 5 days at 20° C.

*Time to initiate roots, winter.*—About 6 days at 18° C.

*Time to produce a rooted cutting, summer.*—About 12 days at 20° C.

*Time to produce a rooted cutting, winter.*—About 14 days at 18° C.

*Root description.*—Fine and freely branching; white in color.

Plant description:

*Appearance.*—Herbaceous anemone-type cut *Chrysanthemum;* typically grown as a spray-type; erect and strong flowering stems.

*Growth rate.*—Rapid; vigorous.

*Flowering stem description.*—Length: About 80 cm. Diameter: About 6 mm. Strength: Strong. Aspect: Erect. Color: 146A.

*Foliage description.*—Arrangement: Alternate. Length: About 7 to 11 cm. Width: About 5 to 8 cm. Apex: Mucronulate. Base: Attenuate. Margin: Pinnately lobed; serrate. Texture, upper and lower surface: Pubescent. Petiole length: About 1.5 to 3 cm. Color: Developing foliage, upper surface: Close to 147A. Developing foliage, lower surface: 137A to 137B. Fully expanded foliage, upper surface: Close to 137A. Fully expanded foliage, lower surface: Close to 147B. Venation, upper and lower surfaces: 146B. Petiole, upper and lower surfaces: 146B to 146C.

Inflorescence description:

*Appearance.*—Anemone-type inflorescence form with elliptic-shaped ray florets. Inflorescences borne on terminals above foliage. Disk and ray florets develop acropetally on a capitulum. Inflorescences not fragrant. Typically grown as a spray-type.

*Flowering response.*—Under natural conditions, plant typically flower in November in the Northern Hemisphere. At other times of the year, inflorescence initiation and development can be induced under short day/long night conditions (at least 13.5 hours of darkness). Plants exposed to long day/short night conditions after planting followed by photoinductive short day/long night conditions flower about 48 days later. Early and uniform flowering response.

*Postproduction longevity.*—Cut inflorescences will maintain good substance and form for about 3.5 weeks.

*Quantity of inflorescences per flowering stem.*—About 23 to 28 inflorescences per flowering stem.

*Inflorescence size.*—Diameter: About 5 to 6 cm. Depth (height): About 1.5 cm. Diameter of disc: About 2.5 cm.

*Inflorescence buds.*—Length: About 5 mm. Diameter: About 9 mm. Shape: Oblate. Color: 137C.

*Ray florets.*—Length: About 3 cm. Width: About 8 mm. Shape: Elliptic. Apex: Retuse. Base: Fused. Margin: Entire. Texture, upper and lower surfaces: Smooth, glabrous; satiny. Number of ray florets per inflorescence: About 27. Color: When opening, upper surface: 155B. When opening, lower surface: 155B; towards the apex, blushed with 62C. Fully opened, upper surface: Close to 155C. Fully opened, lower surface: Close to 155C; towards the apex, blushed with 84B to 84C.

*Disc florets.*—Shape: Tubular; enlarged. Length: About 0.5 to 2 cm. Width: About 1 to 3 mm. Number of disc florets per inflorescence: About 211. Color: Immature: N144D. Mature: Apex: 64A to 64B. Midsection: Close to 155B. Base: N144D.

*Peduncles.*—Length, terminal peduncle: About 3 cm. Length, fourth peduncle: About 7 cm. Diameter: About 2 to 4 mm. Strength: Moderately strong. Angle: About 45° from vertical. Texture: Pubescent. Color: 147B.

*Reproductive organs.*—Androecium: Present on disc florets only. Anther color: Close to 12A. Pollen color: Close to 12A. Gynoecium: Present on both ray and disc florets.

*Seed/fruit.*—Seed and fruit production has not been observed.

Disease/pest resistance: Resistance to known *Chrysanthemum* pathogens and pests has not been observed on plants of the new *Chrysanthemum.*

It is claimed:

1. A new and distinct cultivar of *Chrysanthemum* plant named 'Samos', as illustrated and described.

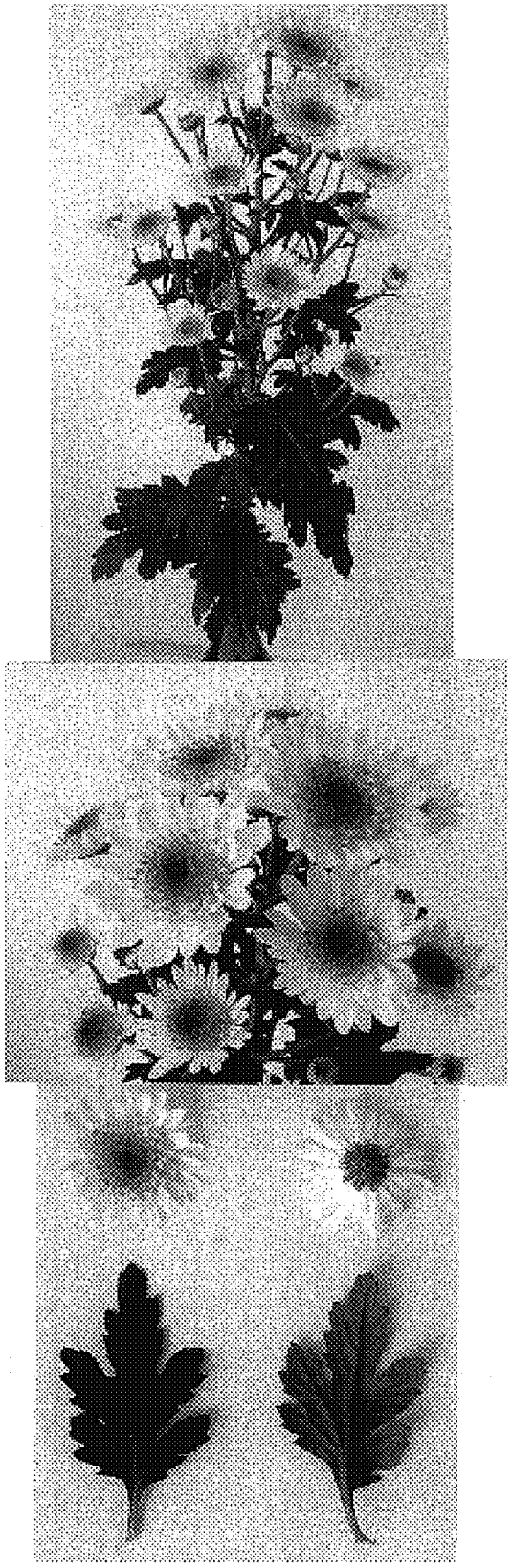

* * * * *